United States Patent
Huang

Patent Number: 5,643,138
Date of Patent: Jul. 1, 1997

[54] ELECTRONIC HAND-MUSCLE DEVELOPER

[76] Inventor: Tien-Tsai Huang, No. 4, Lane 30, Wu-Chang St., Pan-Chiao City, Taiwan

[21] Appl. No.: 579,743

[22] Filed: Dec. 28, 1995

[51] Int. Cl.$^6$ ............................................. A61B 5/11
[52] U.S. Cl. .................. 482/4; 482/3; 482/44; 482/49; 73/379.01; 73/379.09
[58] Field of Search ............................ 482/44, 49, 47, 482/83, 84, 112, 111, 1–9, 900–902, 909; 73/379.01, 379.02, 379.09; 285/239

[56] References Cited

U.S. PATENT DOCUMENTS

| | | | |
|---|---|---|---|
| 4,949,729 | 8/1990 | Haski | 128/774 |
| 5,335,943 | 8/1994 | Duryea | 285/12 |

*Primary Examiner*—Richard J. Apley
*Assistant Examiner*—Glenn E. Richman
*Attorney, Agent, or Firm*—Fish & Richardson P.C.

[57] ABSTRACT

An electronic hand-muscle developer which includes a casing having a connector; a hollow flexible grip filled up with air and connected to the connector; a pressure inductor mounted in the connector to detect pressure from the hollow flexible grip; a pressure converter circuit mounted in the casing and connected to the pressure inductor to converts the pressure signal detected by the pressure inductor into a frequency signal; a microprocessor mounted in the casing to receive the frequency signal from the pressure converter, and to calculate the frequency signal so as to obtain a value; and a liquid crystal display connected to the microprocessor to display the value obtained by the microprocessor.

8 Claims, 3 Drawing Sheets

ELECTRONIC HAND-MUSCLE DEVELOPER

BACKGROUND OF THE INVENTION

The present invention relates to hand-muscle developers, and relates more particularly to an electronic hand-muscle developer which shows the value of the pressure applied by the user.

Various hand-muscle developers have been disclosed, and have appeared on the market. These hand-muscle developers commonly use spring means to produce a resisting force against the pressure applied by the hand of the user. However, conventional hand-muscle developers cannot count and show the value of the pressure and the number of grips applied by the user.

SUMMARY OF THE INVENTION

It is one object of the present invention to provide an electronic hand-muscle developer which shows the pressure applied by the user. It is another object of the present invention to provide an electronic hand-muscle developer which shows the number of grips applied by the user.

According to one aspect of the present invention, the electronic hand-muscle developer comprises a casing having a connector; a hollow flexible grip filled up with air and connected to the connector; a pressure inductor mounted in the connector to detect pressure from the hollow flexible grip; a pressure converter circuit mounted in the casing and connected to the pressure inductor to converts the pressure signal detected by the pressure inductor into a frequency signal; a microprocessor mounted in the casing to receive the frequency signal from the pressure converter, and to calculate the frequency signal so as to obtain a value; and a liquid crystal display connected to the microprocessor to display the value obtained by the microprocessor. According to another aspect of the present invention, the connector has spaced outside annular flanges forced into the neck of the hollow flexible grip to firmly secure the connection between the connector and the hollow flexible grip. According to still another aspect of the present invention, the microprocessor provides three display modes by means of the control of a function key, namely, the current value display mode in which the microprocessor shows through the liquid crystal display the current pressure value detected by the pressure detector, the frequency display mode in which the microprocessor shows through the liquid crystal display the number of grips applied by the user to the hollow flexible grip, and the maximum pressure display mode in which the microprocessor shows through the liquid crystal display the maximum value ever detected by the pressure inductor.

DETAILED DESCRIPTION OF THE PREFERRED EMBODIMENT

Figure 1:
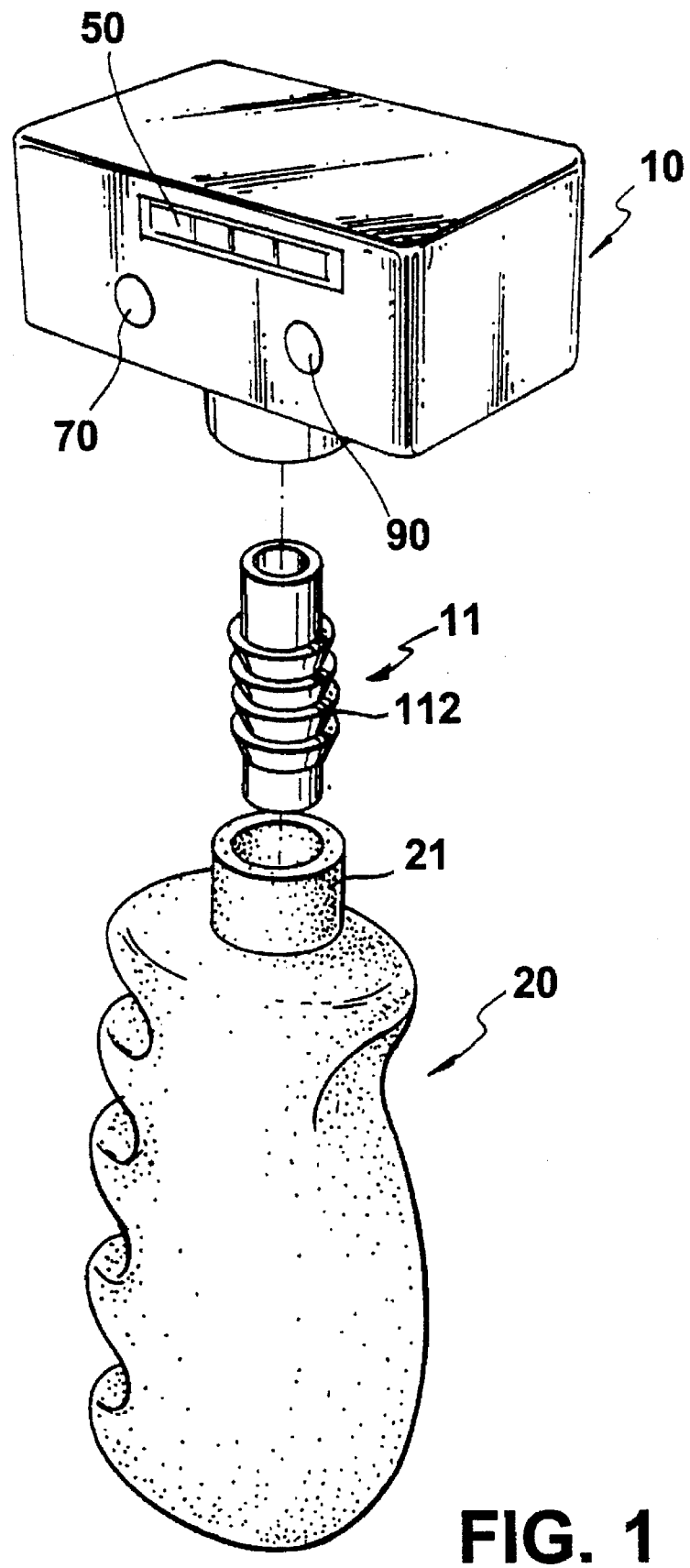
FIG. 1 is an exploded view of an electronic hand-muscle developer according to the present invention.

Referring to FIG. 1, an electronic hand-muscle developer in accordance with the present invention is generally comprised of a casing 10, a tubular connector 11, and a hollow flexible grip 20 connected to the casing 10 by the tubular connector 11. The casing 10 comprises a liquid crystal display 50, a function key 90, and a power switch 70.

Figure 2:
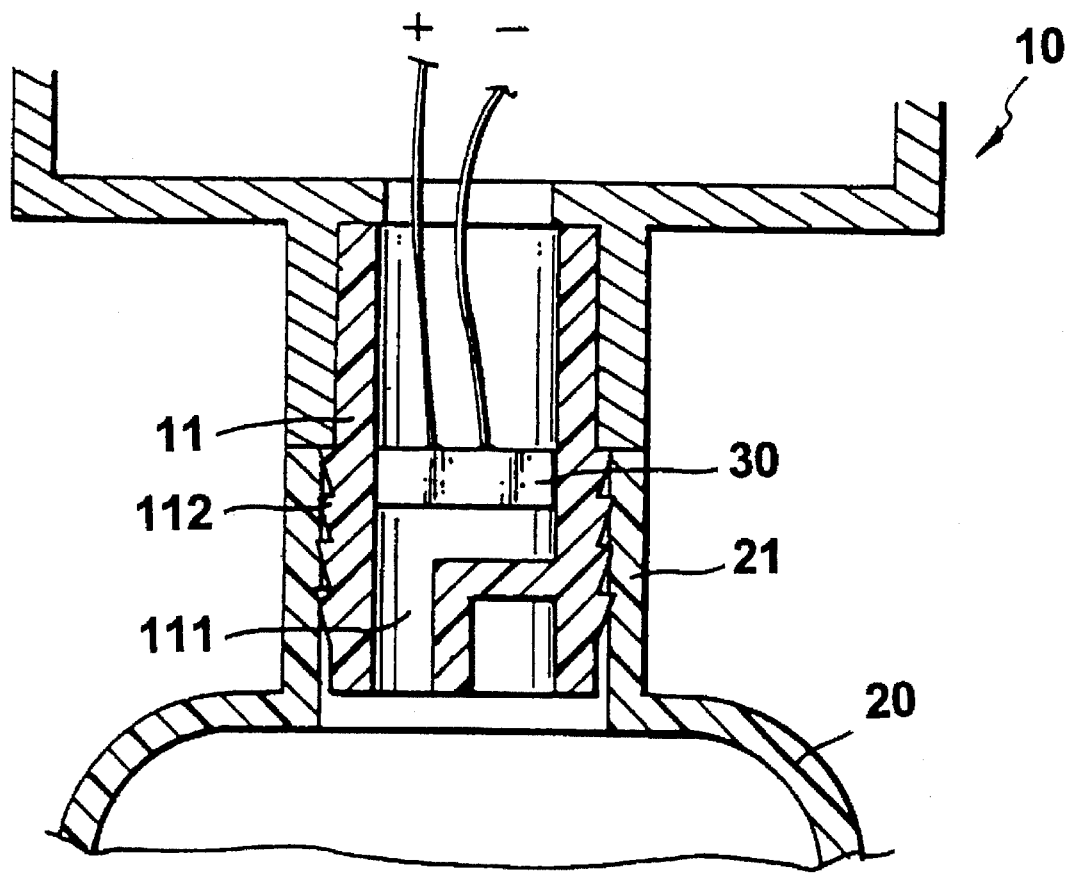
FIG. 2 is a sectional view showing the connector connected between the casing and the hollow flexible grip according to the present invention.

Referring to FIG. 2 and FIG. 1 again, a tubular connector 11 is fixedly secured to the casing 10, having a longitudinal center through hole 111, and a plurality of spaced outside annular flanges 112 forced into engagement with the inside wall of the neck-21 of the hollow flexible grip 20. A pressure inductor 30 is mounted in the longitudinal center through hole 111 of the tubular connector 11. When the hollow flexible grip 20 is squeezed in the hand, a flow of air is driven out of the hollow flexible grip 20 toward the pressure inductor 30.

Figure 3:
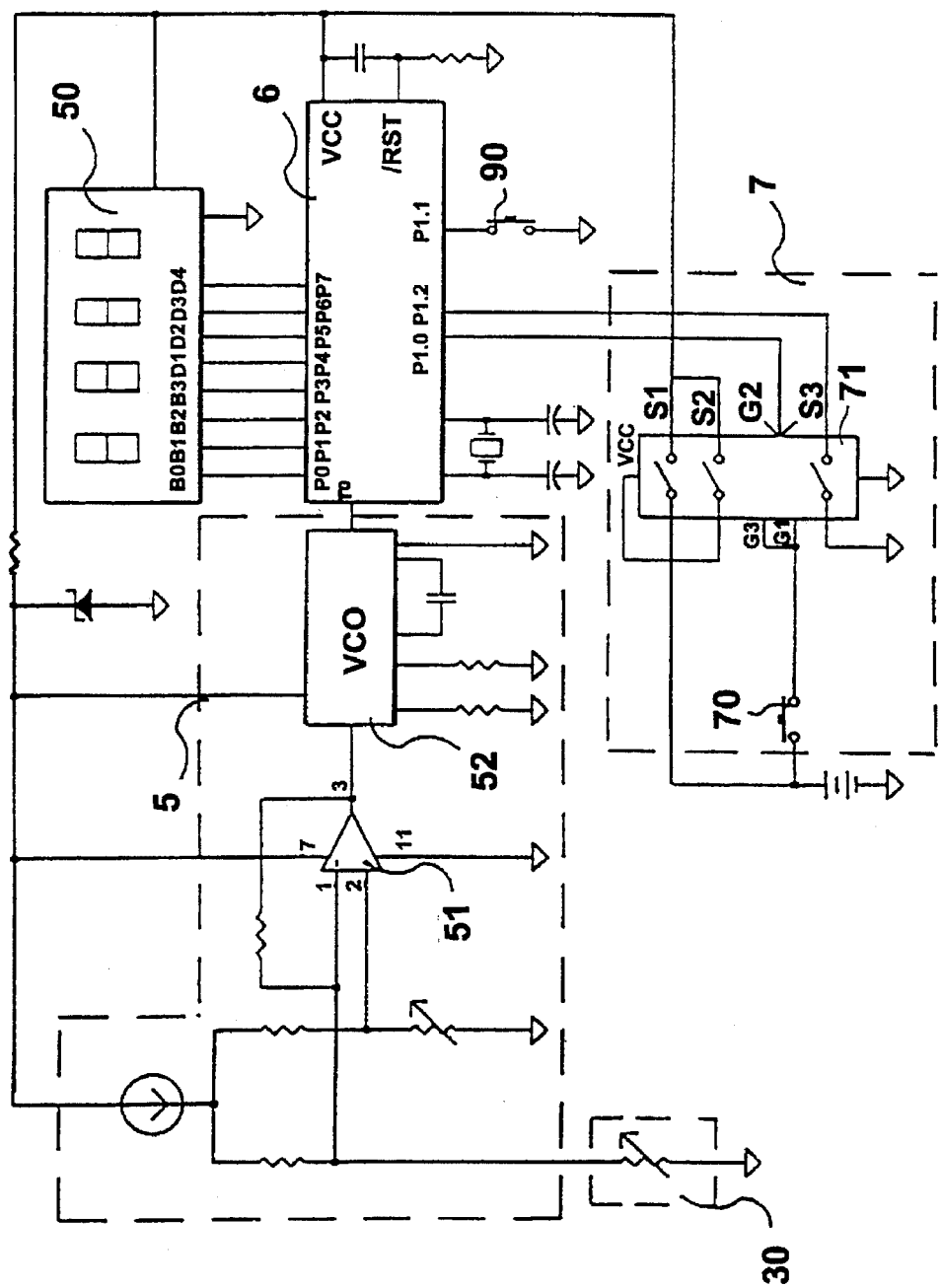
FIG. 3 is a circuit diagram according to the present invention.

Referring to FIG. 3, when the pressure inductor 30 is induced by a pressure to change its impedance, the changing of impedance is amplified by the amplifier 51 of a pressure converter 5, then converted into a corresponding frequency signal by the VCO (voltage control oscillator) 52 of the pressure converter 5, and then the frequency signal is sent to a microprocessor 6 for processing. Because different pressure produces different frequencies. After calculation by the microprocessor 6, a value is obtained corresponding to the frequency signal from the pressure converter 5, and then shown through the liquid crystal display 50. There is a power switch power saving circuit 7 connected to the microprocessor 6. The power switch power saving circuit 7 comprises the aforesaid power switch 70, and a linear switch 71. When the power switch 70 is switched on, power supply is transmitted to the power supply terminal of the microprocessor 6 through the linear switch 71, causing the system started. When the system started, a locking signal is sent to G2 of the linear switch 71 to lock power supply. When the power switch 70 is switched off, the microprocessor 6 immediately cuts off the locking signal from G2, and therefore power supply is turned off. The aforesaid function key 90 is connected to the microprocessor 6 for controlling three functional modes, namely, the current pressure display mode, the maximum pressure display mode, and the frequency display mode. When the function key 90 is switched to the current pressure display mode, the microprocessor 6 shows the value of the current pressure applied to the hollow flexible grip 20 through the liquid crystal display 50. When the function key 90 is switched to the maximum pressure display mode, the microprocessor 6 shows through the liquid crystal display 50 only the value of the maximum pressure detected from the hollow hand grip 20 through the pressure inductor 30, and the reading will be updated only when a higher pressure is detected. When the function key 90 is switched to the frequency display mode, the microprocessor 6 shows through the liquid crystal display 50 the number of grips applied by the user to the hollow flexible grip by: adding one to the reading each time the detected value has surpassed a predetermined value and then dropped below it, i.e., when the hollow flexible grip 20 is squeezed and then immediately released, the microprocessor 6 adds one to reading. Therefore, the number of grips is detected and shown through the liquid crystal display when the user continuously grips the hollow flexible grip 20 and releases it after each gripping.

It is to be understood that the drawings are designed for purposes of illustration only, and are not intended as a definition of the limits and scope of the invention disclosed.

I claim:

1. An electronic hand-muscle developer comprising:

a casing having a connector;

a hollow flexible grip filled with air and connected to said connector;

a pressure inductor mounted in said connector to detect pressure from said hollow flexible grip;

a pressure converter circuit mounted in said casing and connected to said pressure inductor to convert a pressure signal representative of the pressure detected by said pressure inductor into a frequency signal having a variable frequency representative of the detected pressure;

a microprocessor mounted in said casing to receive the frequency signal from said pressure converter, and to calculate a value from the frequency signal; and a liquid crystal display connected to said microprocessor to display the value calculated by said microprocessor.

2. The electronic hand-muscle developer of claim 1 wherein said liquid crystal display is mounted on said casing.

3. The electronic hand-muscle developer of claim 1 wherein said hollow flexible grip has a neck connected to said connector; said connector has one end fixedly secured to said casing, an opposite end formed with spaced-apart external annular flanges which are forced into the neck of said hollow flexible grip, and a longitudinal through-hole extending through both ends to snugly receive said pressure inductor.

4. The electronic hand-muscle developer of claim 1 wherein said microprocessor comprises a display mode controlled by a function key.

5. The electronic hand-muscle developer of claim 4 wherein said display mode is a frequency display mode in which said microprocessor shows through said liquid crystal display the number of grips applied by the user to said hollow flexible grip by: adding one to the reading each time the detected value has surpassed a predetermined value and then dropped below it.

6. The electronic hand-muscle developer of claim 4 wherein said display mode is a maximum pressure display mode in which said microprocessor shows through said liquid crystal display the maximum value detector by said pressure inductor.

7. The electronic hand-muscle developer of claim 1 wherein said pressure converter circuit includes a voltage control oscillator which generates the frequency signal.

8. The electronic hand-muscle developer of claim 7 wherein said pressure converter circuit includes an amplifier, coupled to an input of the voltage control oscillator, to amplify the pressure signal from the pressure inductor.

* * * * *